United States Patent [19]

Gordon

[11] Patent Number: 4,692,455

[45] Date of Patent: Sep. 8, 1987

[54] CERTAIN ACYCLIC, ALICYCLIC, AROMATIC OR HETEROCYCLIC DERIVATIVES OF 3-BENZOYLAMINO-2-OXO-BUTYL-AMINO-CARBONYL-OXY-3-PROPANOIC ACIDS, ESTERS THEREOF, PHARMACEUTICAL COMPOSITIONS CONTAINING SAME AND THEIR ENKEPHALINASE INHIBITING PROPERTIES

[75] Inventor: Eric M. Gordon, Pennington, N.J.

[73] Assignee: E. R. Squibb & Sons, Inc., Princeton, N.J.

[21] Appl. No.: 694,871

[22] Filed: Jan. 25, 1985

[51] Int. Cl.$^4$ .............. C07C 125/04; C07C 149/437; C07D 213/55; A61K 31/44
[52] U.S. Cl. .................................... 514/332; 514/333; 514/336; 514/339; 514/341; 514/342; 514/351; 514/397; 514/412; 514/414; 514/438; 514/444; 514/471; 514/478; 560/16; 560/24; 560/29; 560/34; 560/115; 560/116; 560/159; 558/239; 549/59; 549/60; 549/473; 548/336; 548/342; 548/467; 546/265; 546/273; 546/278; 546/283; 546/284; 546/291
[58] Field of Search .................. 549/59, 60, 473; 548/342, 336, 467; 546/265, 273, 278, 281, 283, 284, 291; 558/239; 564/185, 186, 177, 179, 183, 184; 560/16, 24, 29, 34; 514/332, 333, 336, 339, 342, 397, 412, 414, 438, 444, 471, 478

[56] References Cited

U.S. PATENT DOCUMENTS

| 4,470,973 | 9/1984 | Natarajan et al. ................ 514/19 |
| 4,523,729 | 11/1986 | Natarajan ........................ 546/256 |
| 4,621,092 | 11/1986 | Natarajan ........................ 514/343 |

FOREIGN PATENT DOCUMENTS 17203 1/1984 Australia .............................. 548/467

OTHER PUBLICATIONS

Burger, Medicinal Chemistry, Second Edition, pp. 565–571, 578–581, 600–601, Interscience Publishers, (1960).

*Primary Examiner*—Alan L. Rotman
*Attorney, Agent, or Firm*—Lawrence S. Levinson; Stephen B. Davis

[57] ABSTRACT

Compounds of the formula

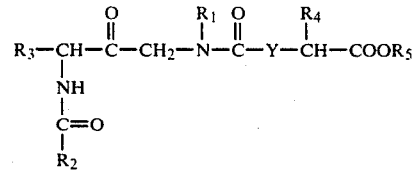

wherein Y is oxygen or sulfur are disclosed. These compounds are useful as hypotensive agents due to their angiotensin converting enzyme inhibition activity and depending upon the definition of $R_1$ may also be useful as analgesics due to their enkepahlinase inhibition activity.

10 Claims, No Drawings

CERTAIN ACYCLIC, ALICYCLIC, AROMATIC OR HETEROCYCLIC DERIVATIVES OF 3-BENZOYLAMINO-2-OXO-BUTYL-AMINO-CARBONYL-OXY-3-PROPANOIC ACIDS, ESTERS THEREOF, PHARMACEUTICAL COMPOSITIONS CONTAINING SAME AND THEIR ENKEPHALINASE INHIBITING PROPERTIES

BACKGROUND OF THE INVENTION

Natarajan et al. in Australian Patent Application No. 17,203 discloses acylaminocarbonyl substituted amino and imino acids and esters which possess angiotensin converting enzyme inhibition activity and enkephalinase inhibition activity.

SUMMARY OF THE INVENTION

This invention is directed to novel acylaminoalkanoyl compounds of the formula $$R_3-\overset{*}{C}H-\overset{O}{\underset{\|}{C}}-CH_2-\overset{R_1}{\underset{|}{N}}-\overset{O}{\underset{\|}{C}}-Y-\overset{R_4}{\underset{|}{\overset{*}{C}H}}-COOR_5 \quad (I)$$
$$\underset{|}{NH}$$
$$\underset{|}{C=O}$$
$$\underset{|}{R_2}$$

Y is oxygen or sulfur.
$R_1$ is hydrogen, lower alkyl,

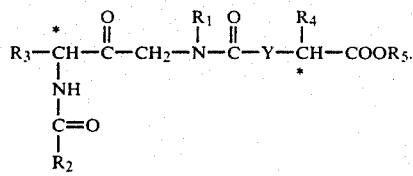

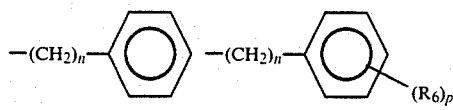

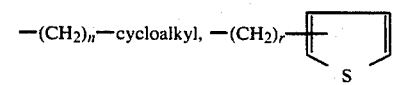

$R_2$ is hydrogen, lower alkyl,

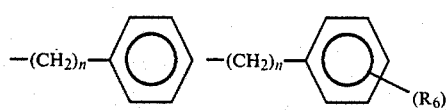

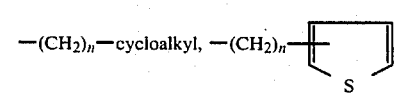

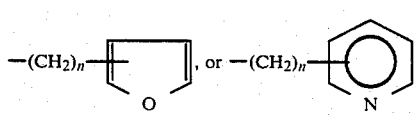

$R_3$ is hydrogen, lower alkyl,

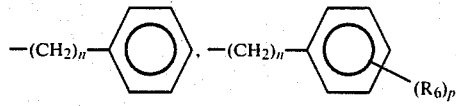

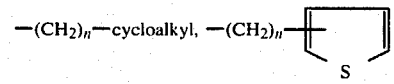

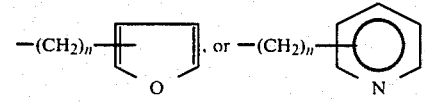

$R_4$ is hydrogen, lower alkyl,

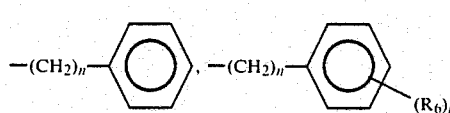

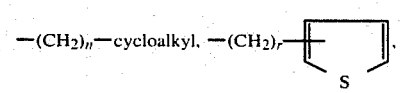

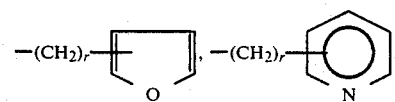

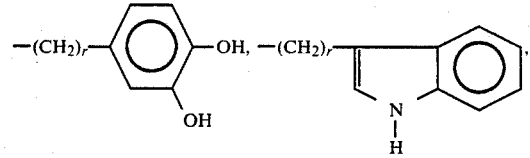

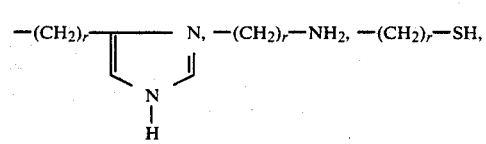

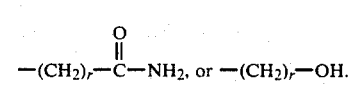

$R_5$ is hydrogen, lower alkyl, benzyl, benzhydryl, salt forming ion, or

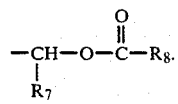

$R_6$ is hydrogen, lower alkyl of 1 to 4 carbons, lower alkoxy of 1 to 4 carbons, lower alkylthio of 1 to 4 carbons, chloro, bromo, fluoro, trifluoromethyl, or hydroxy.

n is zero, one, two, three or four.
r is one, two, three, or four.

p is one, two or three provided that p is more than one only if $R_6$ is methyl, methoxy, methylthio, chloro, or fluoro.

$R_7$ is hydrogen, lower alkyl, cycloalkyl, or phenyl.

$R_8$ is hydrogen, lower alkyl, lower alkoxy, or phenyl.

DETAILED DESCRIPTION OF THE INVENTION

This invention is directed to the various novel acylaminoalkanoyl compounds of formula I above, and compositions and methods of using compositions containing these novel compounds.

The term lower alkyl used in defining various symbols refers to straight or branched chain radicals having up to seven carbons. The preferred lower alkyl groups are up to four carbons with methyl and ethyl most preferred. Similarly, the terms lower alkoxy and lower alkylthio refer to such lower alkyl groups attached to an oxygen or sulfur.

The term cycloalkyl refers to saturated rings of 3 to 7 carbon atoms with cyclopentyl and cyclohexyl being most preferred.

The symbols

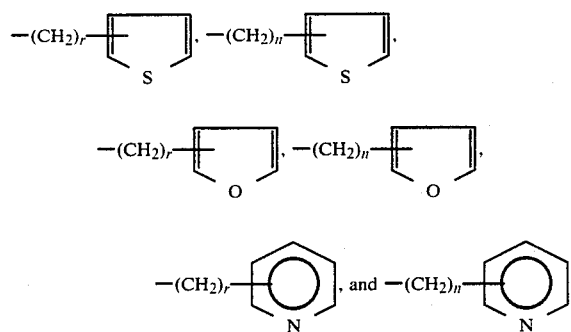

represent that the alkylene bridge is attached to an available carbon atom.

The compounds of formula I can be prepared by reacting an alcohol or mercaptan of the formula

wherein $R_5$ is an ester protecting group, with an aminoketone of the formula

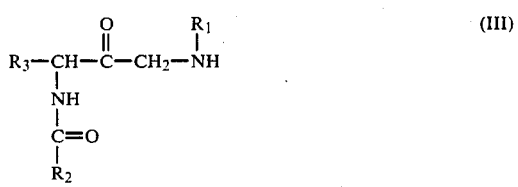

particularly the hydrochloride salt thereof in the presence of phosgene. One of the reactants is first converted to an activated form by treatment with phosgene and then the reaction is performed in the presence of N-methylmorpholine.

The intermediate of formula II wherein Y is oxygen can be prepared by reacting an α-amino

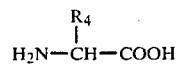

with sulfuric acid followed by the dropwise addition of sodium nitrite to give the alcohol of the formula

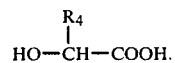

The alcohol of formula V is then treated to convert the carboxylic acid to the desired ester by conventional means. For example, when $R_5$ is ethyl the alcohol of formula V is treated with p-toluenesulfonic acid and ethanol.

The intermediates of formula II wherein Y is sulfur can be prepared by reacting an α-amino acid of formula IV with sulfuric acid, sodium nitrite and sodium bromide to give the bromide of the formula

The bromide of formula VI is then treated to convert the carboxylic acid to the desired ester by conventional means. For example, when $R_5$ is ethyl the bromide of formula VI is treated with ethanol in the presence of dicyclohexylcarbodiimide.

This ester is then treated with thioacetic acid, followed by ammonia to give the desired intermediate of formula II.

The acylated alkylamine of formula III can be prepared by converting a carboxyalkylamine of the formula

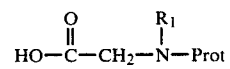

wherein Prot is a protecting group such as benzyloxycarbonyl, to its acid chloride and then reacting with an oxazolone of the formula

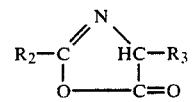

to yield

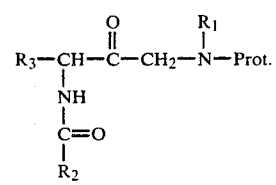

Removal of the protecting group such as by hydrogenation yields the reactant of formula III.

The reactant of formula III wherein $R_1$ is other than hydrogen can also be prepared by reacting a ketone of the formula

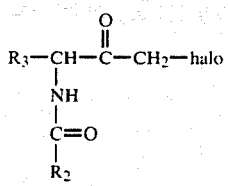 (X)

wherein halo is Cl or Br with a substituted amine of the formula
(XI)

The ketone intermediate of formula X can be prepared by treating a ketone of the formula

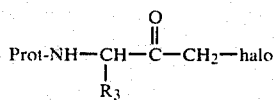 (XII)

wherein Prot is a protecting group such as benzyloxycarbonyl with hydrogen bromide and acetic acid followed by reaction with the acid halide of the formula

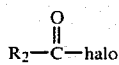 (XIII)

in the presence of base such as sodium bicarbonate.

In the above reactions if $R_6$ is hydroxy or $R_4$ is —$(CH_2)_r$—OH,

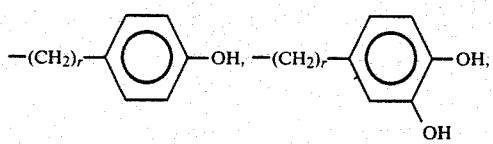

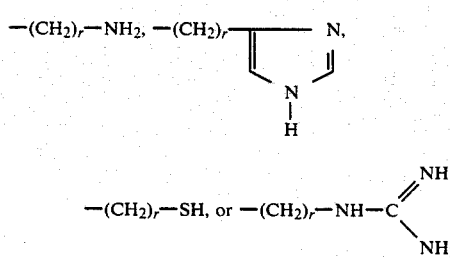

then the hydroxy, amino, imidazolyl, mercaptan or guanidinyl function should be protected during the reaction. Suitable protecting groups include benzyloxycarbonyl, t-butoxycarbonyl, benzyl, benzhydryl, trityl, etc., and nitro in the case of guanidinyl. The protecting group is removed by hydrogenation, treatment with acid, or other known means following completion of the reaction.

The ester products of formula I wherein $R_5$ is lower alkyl, benzyl, or benzhydryl can be chemically treated such as with sodium hydroxide in methanol to yield the products of formula I wherein $R_5$ is hydrogen. The benzyl and benzhydryl esters can also be hydrogenated, for example, by treating with hydrogen in the presence of palladium catalyst.

The ester products of formula I wherein $R_5$ is

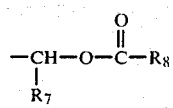

can be obtained by employing the alcohol or mercaptan of formula II in the above reactions with such ester group already in place. These ester products can also be obtained by treating the product of formula I wherein $R_5$ is hydrogen with a molar excess of the compound of the formula

 (XIV)

wherein L is a leaving group such as chlorine, bromine, tolylsulfonyl, etc.

Preferred compounds of this invention are those wherein:

$R_1$ is straight or branched chain lower alkyl of 1 to 4 carbons,

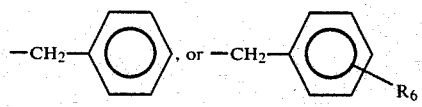

wherein $R_6$ is methyl, methoxy, methylthio, hydroxy, Cl, Br, or F.

$R_2$ is

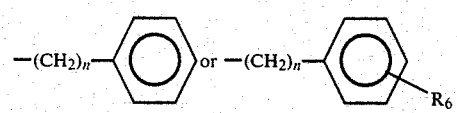

wherein n is zero, one or two and $R_6$ is methyl, methoxy, methylthio, hydroxy, Cl, Br, or F.

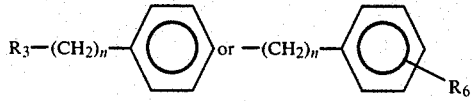

wherein n is zero, one or two and $R_6$ is methyl, methoxy, methylthio, hydroxy, Cl, Br, or F.

$R_4$ is straight or branched chain lower alkyl of 1 to 4 carbons, —$(CH_2)_4$—$NH_2$, —$CH_2$—OH,

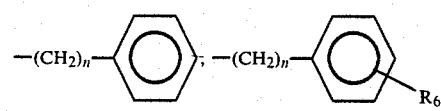

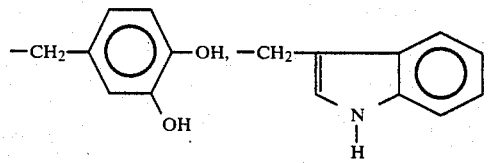

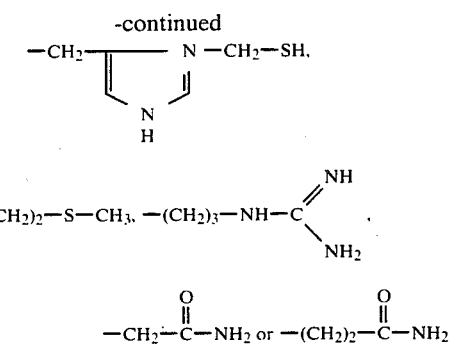

wherein n is zero, one or two and $R_6$ is methyl, methoxy, methylthio, hydroxy, Cl, Br, or F.

$R_5$ is hydrogen, an alkali metal salt, straight or branched chain lower alkyl of 1 to 4 carbons, or

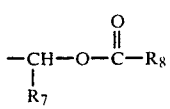

wherein $R_7$ is hydrogen, straight or branched chain lower alkyl of 1 to 4 carbons, or cyclohexyl and $R_8$ is straight or branched chain lower alkyl of 1 to 4 carbons or phenyl.

Most preferred compounds of this invention are those of formula I wherein:
Y is oxygen.
$R_1$ is methyl.
$R_2$ is phenyl.
$R_3$ is benzyl.
$R_4$ is benzyl.
$R_5$ is hydrogen or an alkali metal salt ion.

The compounds of formula I wherein $R_5$ is hydrogen form salts with a variety of inorganic or organic bases. The nontoxic, pharmaceutically acceptable salts are preferred, although other salts are also useful in isolating or purifying the product. Such pharmaceutically acceptable salts include alkali metal salts such as sodium, potassium or lithium, alkaline earth metal salts such as calcium or magnesium, and salts derived from amino acids such as arginine, lysine, etc. The salts are obtained by reacting the acid form of the compound with an equivalent of the base supplying the desired ion in a medium in which the salt precipitates or in aqueous medium and then lyophilizing.

As shown above, the compounds of formula I contain two asymmetric centers represented by the * when $R_3$ and $R_4$ are other than hydrogen. Thus, the compounds of formula I can exist in diastereomeric forms or in mixtures thereof. The above described processes can utilize racemates, enantiomers or diastereomers as starting materials. When diastereomeric products are prepared, they can be separated by conventional chromatographic or fractional crystallization methods.

The compounds of formula I, and the pharmaceutically acceptable salts thereof, are hypotensive agents. They inhibit the conversion of the decapeptide angiotensin I to angiotensin II and, therefore, are useful in reducing or relieving angiotensin related hypertension. The action of the enzyme renin on angiotensinogen, a pseudoglobulin in blood, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention intervene in the angiotensinogen→(renin)→angiotensin I→angiotensin II sequence by inhibiting angiotensin converting enzyme and reducing or eliminating the formation of the pressor substance angiotensin II. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 0.1 to 100 mg., preferably about 1 to 50 mg., per kilogram of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in an effective amount which comprises a total daily dosage of about 30 to 600 mg., preferably about 30 to 330 mg. of a compound of this invention, and about 15 to 300 mg., preferably about 15 to 200 mg. of the diuretic, to a mammalian species in need thereof. Exemplary of the diuretics contemplated for use in combination with a compound of this invention are the thiazide diuretics, e.g., chlorothiazide, hydrochlorothiazide, flumethiazide, hydroflumethiazide, bendroflumethiazide, methyclothiazide, trichloromethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration, or in sterile solutions or suspensions for parenteral administration. About 10 to 500 mg. of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The compounds of formula I wherein $R_1$ is branched chain lower alkyl of 3 or 4 carbons,

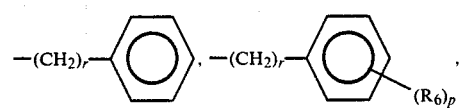

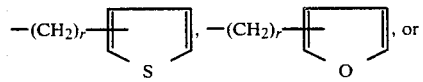

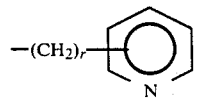

also possess enkephalinase inhibition activity and are useful as analgesic agents. Thus, by the administration of a composition containing one or a combination of such compounds of formula I or a pharmaceutically acceptable salt thereof, pain is alleviated in the mammalian host. A single dose, or preferably two to four divided daily doses, provided on a basis of about 0.1 to about 100 mg. per kilogram of body weight per day, preferably about 1 to about 50 mg. per kilogram per day, produces the desired analgesic activity. The composition is preferably administered orally but parenteral routes such as subcutaneous can also be employed.

The following examples are illustrative of the invention. Temperatures are given in degrees centigrade.

EXAMPLE 1

(S)-2-[[[[3-(Benzoylamino)-2-oxo-4-phenylbutyl]methylamino]carbonyl]oxy]-3-phenylpropanoic acid (a) (S)-2-Hydroxy-3-phenylpropanoic acid 1N Hydrochloric acid (600 ml.) is added to a stirred suspension of L-phenylalanine (100 g., 0.60 mole) in water (350 ml.). After cooling to 0°, 10% sulfuric acid (900 ml.) is added followed by the dropwise addition over a period of two hours of a solution of sodium nitrite (90 g., 1.30 mole) in water (480 ml.). After stirring overnight at room temperature, the resulting solution is extracted with ether (2×2 l.). The extracts are combined and dried (MgSO$_4$). The solvent is removed at reduced pressure and the residue is treated with benzene to give 72.5 g. of solid (S)-2-hydroxy-3-phenylpropanoic acid. Recrystallization from benzene gives 61.66 g. of colorless (S)-2-hydroxy-3-phenylpropanoic acid, m.p. 123°-125°; $[\alpha]_D^{20} = -26.9°$ (c=1.11, acetone). TLC (silica gel; benzene:acetone, 1:1) R$_f$=0.47.

(b) (S)-2-Hydroxy-3-phenylpropanoic acid, ethyl ester.

A 1 l. flask equipped with a soxlet extractor, reflux condenser, and a drying tube is charged with (S)-2-hydroxy-3-phenylpropanoic acid (63.5 g., 0.38 mole), p-toluenesulfonic acid (0.61 g.) and absolute ethanol (700 ml.). The soxlet is charged with 3 A° molecular sieves. After heating at reflux for six hours, the soxlet is recharged with fresh sieves and the heating is continued for 14 hours. The mixture is cooled and the bulk of slvent is removed at reduced pressure. The residue is dissolved in ether (800 ml.) and washed with 1N sodium bicarbonate and brine. After drying (MgSO$_4$), the solvent is removed at reduced pressure to give 71.26 g. of (S)-2-hydroxy-3-phenylpropanoic acid, ethyl ester as a light yellow solid.

(c) (S)-3-Amino-1-chloro-4-phenyl-2-butanone, hydrogen bromide (S)-[3-Chloro-2-oxo-1-(phenylmethyl)propyl]carbamic acid, phenylmethyl ester (51.4 g.) is dissolved in a mixture of acetic acid (252 ml.) and hydrogen bromide in acetic acid (3.45N, 348 ml.) and kept at room temperature for 1.5 hours. The reaction mixture is then concentrated in vacuo and precipitated with ether to obtain 36.6 g. of (S)-3-amino-1-chloro-4-phenyl-2-butanone, hydrogen bromide; m.p. (175°) 177°-179°.

(d) (S)-N-[3-Chloro-2-oxo-1-(phenylmethyl)propyl]benzamide (S)-3-Amino-1-chloro-4-phenyl-2-butanone, hydrogen bromide (36.6 g., 130.3 mmole) is suspended in 520 ml. of dry tetrahydrofuran and 18.2 ml. of triethylamine (130.3 mmole) with stirring for ten minutes. The mixture is placed in an ice bath and 15.2 ml. of benzoyl chloride is added followed by 10.95 g. of sodium bicarbonate. After 5 minutes the ice bath is removed and the reaction mixture is kept at room temperature for 1.5 hours. The reaction mixture is then concentrated in vacuo and the residue taken up in 1 l. of aqueous methanol (10% water). The precipitate is collected, filtered and washed with methanol to obtain 25.3 g. of (S)-N-[3-chloro-2-oxo-1-(phenylmethyl)propyl]benzamide; m.p. (160°) 170°-172° (dec.); $[\alpha]_D^{20} = -129°$ (c=1.7, dimethylformamide).

(e) (S)-N-[3-Methyl(phenylmethyl)amino]-2-oxo-1-(phenylmethyl)propyl]benzamide

Benzylmethylamine (1.28 ml., 0.75 eq.) is added to a stirred suspension of (S)-N-[3-chloro-2-oxo-1-(phenylmethyl)propyl]benzamide (4.0 g., 13.2 mmole), sodium iodide (2.0 g., 2 eq.) and sodium bicarbonate (1.12 g., 1 eq.) in dry dimethylformamide (25 ml.) under argon. The resulting mixture is stirred at room temperature for 1.5 hours and then diluted with ether. After washing with water (twice), the organic phase is extracted with 0.5N hydrochloric acid (3×100 ml.). The hydrochloric acid fractions are combined and back extracted with ether and the organic fractions are discarded. The hydrochloric acid fraction is basified with sodium bicarbonate (20 g.) and extracted with ethyl acetate. The ethyl acetate fraction is washed with water and brine. After drying over anhydrous MgSO$_4$, the solvent is removed at reduced pressure to give 2.46 g. of (S)-N-[3-[methyl(phenylmethyl)amino]-2-oxo-1-(phenylmethyl)propyl]benzamide as a light yellow solid. TLC (silica gel, ethyl acetate) R$_f$=0.50.

(f) (S)-N-[3-(Methylamino)-2-oxo-1-(phenylmethyl)propyl]benzamide, hydrochloride A mixture of N-[3-[methyl(phenylmethyl)amino]-2-oxo-1-(phenylmethyl)propyl]benzamide (2.4 g., 6.32 mmole), 10 ml. of 1N hydrochloric acid (1.5 eq.) and palladium hydroxide on carbon catalyst (410 mg.) in 95% ethanol (90 ml.) is stirred under hydrogen (balloon). After stirring for 2 hours, the mixture is filtered (millipore) and the filtrate is concentrated at reduced pressure. The residue is chased once with absolute ethanol and the resulting material is washed with ether and dried under vacuum to give 1.95 g. of (S)-N-[3-(methylamino)-2-oxo-1-(phenylmethyl)propyl]benzamide, hydrochloride; $[\alpha]_D^{20} = -106.3°$ (c=1.04, methanol).

(g) (S)-2-[[[[3-Benzoylamino)-2-oxo-4-phenylbutyl]methylamino]carbonyl]oxy]-3-phenylpropanoic acid, ethyl ester A 12.5% solution of phosgene in benzene (10.0 ml., 95 mmole) is added with stirring to a solution of (S)-2-hydroxy-3-phenylpropanoic acid, ethyl ester (1.75 g., 9 mmole) in methylene chloride (30 ml., distilled) and N-methylmorpholine (1.0 ml., 9 mmole) at −20°. After stirring at −20° under nitrogen for 30 minutes and at room temperature for 45 minutes, the reaction mixture is concentrated under reduced pressure and the residue is chased once with methylene chloride (10 ml.). The residue is suspended in methylene chloride (30 ml.) and treated with a suspension of (S)-N-[3-(methylamino)-2- oxo-1-(phenylmethyl)propyl]benzamide, hydrochloride (2.0 g., 6 mmole) and N-methylmorpholine (1.66 ml., 15 mmole) in methylene chloride (30 ml.). After stirring at room temperature overnight, the reaction mixture is concentrated at reduced pressure. The residue is redissolved in ethyl acetate (100 ml.) and washed with water (twice), saturated sodium bicarbonate (twice), potassium bisulfate (twice), dried (Na$_2$SO$_4$), and concentrated into a pale brown oil which solidifies upon drying in high vacuum. The crude product (3.7 g.) is recrystalized from warm ethyl acetate/hexane to yield 2.1 g. of (S)-2-[[[[3-benzoylamino)-2-oxo-4-phenylbutyl]methylamino]carbonyl]oxy]-3-phenylpropanoic acid, ethyl ester as a white solid. TLC (silica gel; 15% ethyl acetate/methylene chloride) R$_f$=0.37.

(h) (S)-2-[[[[3-(Benzoylamino)-2-oxo-4-phenylbutyl]methylamino]carbonyl]oxy]-3-phenylpropanoic acid Tetrahydrofuran (5 ml.) is added to a suspension of the ethyl ester product from part (g) (1.03 g., 2 mmole) in methanol/water (20 ml./2ml.) until a clear solution is obtained. This solution is cooled to 0° and 1N sodium hydroxide is added (2.1 ml., 2.1 mmole). After stirring overnight (0° to room temperature), the reaction mixture is concentrated to 1/3 volume, diluted with saturated sodium bicarbonate (30 ml.) and extracted with ethyl acetate (three times). The combined ethyl acetate extracts are dried (Na$_2$SO$_4$) and concentrated under reduced pressure into a yellow foam (1.09 g.). Purification by flash chromatography (Whatman LPS-1 silica gel, 20% ethyl acetate/methylene chloride and 1:1:1 chloroform/methnaol/acetic acid) gives 0.61 g. of (S)-2-[[[[3-(benzoylamino)-2-oxo-4-phenylbutyl]methylamino]carbonyl]oxy]-3-phenylpropanoic acid; m.p. 52°–60°. TLC (silica gel; chloroform:methanol:acetic acid; 18:1:1) R$_f$=0.42.

Anal. calc'd. for C$_{28}$H$_{28}$N$_2$O$_6$.0.5H$_2$O: C, 67.59; H, 5.88; N, 5.63. Found: C, 67.50; H, 5.77; N, 5.41.

EXAMPLES 2–20

Following the procedures of Example 1 but employing the alcohol or mercaptan shown below in Col. I and the acylated alkylamine shown below in Col. II, one obtains the ester product shown in Col. III. Removal of the ester group yields the corresponding product as the carboxylic acid, i.e., R$_5$ is hydrogen.

Col. I

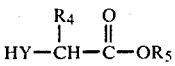

Col. II

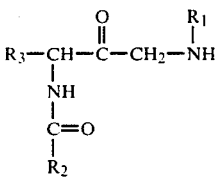

Col. III

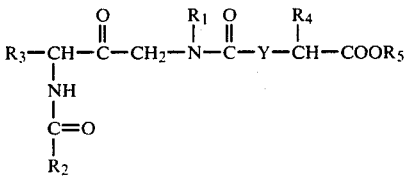

| Example | $R_1$ | $R_2$ | $R_3$ | Y | $R_4$ | $R_5$ |
|---|---|---|---|---|---|---|
| 2 | —$CH_3$ | —C₆H₅ | —$CH_2$—C₆H₅ | S | —$CH_2$—C₆H₅ | —$C_2H_5$ |
| 3 | —$CH_2$—C₆H₅ | —C₆H₄(OCH₃) | —$CH_2$—C₆H₄(F) | O | —$CH_2$—C₆H₅ | —$C_2H_5$ |
| 4 | —CH(CH₃)₂ | —C₆H₅ | —$CH_2$—C₆H₄(CH₃) | S | —$CH_2$—C₆H₅ | —$C_2H_5$ |
| 5 | —$CH_3$ | —$CH_2$—C₆H₅ | —C₆H₅ | O | —$CH_2$—(Pyridyl) | —$C_2H_5$ |
| 6 | —$CH_2$—C₆H₁₁ | —(Pyridyl) | —$CH_2$—C₆H₅ | S | —$(CH_2)_2$—C₆H₅ | —$C_2H_5$ |
| 7 | —$CH_3$ | —C₆H₅ | —$CH_2$—(thienyl) | S | —$CH_2$—C₆H₅ | —$C_2H_5$ |
| 8 | —$CH_3$ | —C₆H₁₁ | —$CH_2$—(furyl) | O | —$(CH_2)_3$—NH—C(=NH)—NH—NO₂ | —$C_2H_5$ |
| 9 | —$CH_3$ | —$(CH_2)_3$—C₆H₅ | —$CH_2$—C₆H₁₁ | O | —$(CH_2)_4$—NH—C(=O)—O—$CH_2$—C₆H₅ | —$CH_2$—C₆H₅ |

-continued

| Example | R₁ | R₂ | R₃ | Y | R₄ | R₅ |
|---|---|---|---|---|---|---|
| 10 | —CH₃ | 4-(S—CH₃)-phenyl | —CH₂-phenyl | O | 4-(phenyl-CH₂O)-phenyl | —CH₂-phenyl |
| 11 | —CH₃ | —CH(CH₃)₂ | —CH₂-phenyl | O | 3-(phenyl-CH₂O)-, 2-(phenyl-OCH₂)-phenyl | —CH₂-phenyl |
| 12 | —CH₃ | —C₂H₅ | —CH₂-phenyl | O | —CH₂—CH=N—CH₂-phenyl | —CH₂-phenyl |
| 13 | —CH₃ | phenyl | —CH₂-phenyl | O | —CH₂—(2-(NH)-phenyl) | —C₂H₅ |
| 14 | —CH₂-(2-thienyl) | phenyl | —CH₂-phenyl | S | —CH₂-phenyl | —C₂H₅ |
| 15 | —(CH₂)₂-(2-pyridyl) | phenyl | —CH₂-phenyl | O | —CH₂-phenyl | —C₂H₅ |
| 16 | phenyl | phenyl | —CH₂-(2-pyridyl) | S | —CH₂-phenyl | —C₂H₅ |

-continued

| Example | $R_1$ | $R_2$ | $R_3$ | Y | $R_4$ | $R_5$ |
|---|---|---|---|---|---|---|
| 17 | —CH$_2$CH(CH$_3$)$_2$ | —C$_6$H$_5$ | —CH$_2$—C$_6$H$_5$ | O | —CH$_2$—C$_6$H$_5$ | —CH$_2$—C$_6$H$_5$ |
| 18 | —CH$_3$ | —C$_6$H$_5$ | —CH$_2$—C$_6$H$_5$ | S | —CH$_2$—C$_6$H$_5$ | —CH(C$_6$H$_{11}$)—O—C(O)—C$_2$H$_5$ |
| 19 | —CH$_2$—C$_6$H$_5$ | —C$_6$H$_5$ | —CH$_2$—C$_6$H$_5$ | O | —CH$_2$—C$_6$H$_5$ | —CH(CH(CH$_3$)$_2$)—O—C(O)—C$_2$H$_5$ |
| 20 | —CH$_2$—C$_6$H$_5$ | —C$_6$H$_5$ | —CH$_2$—C$_6$H$_5$ | S | —CH$_2$—C$_6$H$_5$ | —CH$_2$—O—C(O)—C(CH$_3$)$_3$ |

The R₄ protecting groups in Examples 8 to 12 are removed as the last step in the synthesis. The R₅ ester groups in Examples 18 to 20 are not removed.

EXAMPLE 21

(S)-2-[[[[3-Benzoylamino)-2-oxo-4-phenylbutyl]methylamino]carbonyl]oxy]-3-phenylpropanoic acid, sodium salt (S)-2-[[[[3-(Benzoylamino)-2-oxo-4-phenylbutyl]methylamino]carbonyl]oxy-3-phenylpropanoic acid (1 mmole) is dissolved in water (50 ml.). Aqueous sodium bicarbonate (0.1N, 20 ml.) is added and the aqueous solution is lyophilized. It is then dissolved in water (10 ml.) and applied on a column of Sephadex chromatography gel G-10 and eluted with water. Fractions containing the desired product are pooled and lyophilized to give (S)-2-[[[[3-(benzoylamino)-2-oxo-4-phenylbutyl]-methylamino]carbonyl]oxy]-3-phenylpropanoic acid, sodium salt.

EXAMPLE 22

1000 tablets each containing the following ingredients:

| | |
|---|---|
| (S)—2-[[[[3-(Benzoylamino)-2-oxo-4-phenylbutyl]methylamino]carbonyl]oxy]-3-phenylpropanoic acid, sodium salt | 100 mg. |
| Cornstarch | 50 mg. |
| Gelatin | 7.5 mg. |
| Avicel(microcrystalline cellulose) | 25 mg. |
| Magnesium stearate | 2.5 mg. |
| | 185 mg. | are prepared from sufficient bulk quantities by mixing the (S)-2-[[[[3-(benzoylamino)-2-oxo-4-phenylbutyl]methylamino]carbonyl]oxy]-3-phenylpropanoic acid, sodium salt and cornstarch with an aqueous solution of the gelatin. The mixture is dried and ground to a fine powder. The Avicel and then the magnesium stearate are admixed with granulation. The mixture is then compressed in a tablet press to form 1000 tablets each containing 100 mg. of active ingredient.

In a similar manner, tablets containing 100 mg. of the product of any of examples 1 to 20 can be prepared.

A similar procedure can be employed to form tablets containing 50 mg. of active ingredient.

EXAMPLE 23

Two piece #1 gelatin capsules each containing 50 mg. of (S)-2-[[[[3-(benzoylamino)-2-oxo-4-phenylbutyl]methylamino]carbonyl]oxy]-3-phenylpropanoic acid, sodium salt are filled with a mixture of the following ingredients:

| | |
|---|---|
| (S)—2-[[[[3-(Benzoylamino)-2-oxo-4-phenylbutyl]methylamino]carbonyl]oxy]-3-phenylpropanoic acid, sodium salt | 50 mg. |
| Magnesium stearate | 7 mg. |
| Lactose | 193 mg. |
| | 250 mg. |

In a smilar manner capsules containing 50 mg. of the product of any of Examples 1 to 20 can be prepared.

EXAMPLE 24

An injectable solution is prepared as follows:

| | |
|---|---|
| (S)—2-[[[3-(Benzoylamino)-2-oxo-4-phenylbutyl]methylamino]carbonyl]oxy]-3-phenylpropanoic acid, sodium salt | 500 g. |
| Methyl paraben | 5 g. |
| Propyl paraben | 1 g. |
| Sodium chloride | 25 g. |
| Water for injection | 5 l. |

The active substance, preservative, and sodium chloride are dissolved in 3 l. of water for injection and then the volume is brought up to 5 liters. The solution is aseptically filled into presterilized vials which are closed with presterilized rubber closures. Each vial contains 5 ml. of solution in a concentration of 100 mg. of active ingredient per ml. of solution for injection.

In a similar manner, an injectable solution containing 100 mg. of active ingredient per ml. of solution can be prepaed for the product of any of Examples 1 to 20.

EXAMPLE 25

1000 tablets each containing the following ingredients:

| | |
|---|---|
| (S)—2-[[[[3-(Benzoylamino)-2-oxo-4-phenylbutyl]methylamino]carbonyl]oxy]-3-phenylpropanoic acid, sodium salt | 100 mg. |
| Avicel | 100 mg. |
| Hydrochlorothiazide | 12.5 mg. |
| Lactose | 113 mg. |
| Cornstarch | 17.5 mg. |
| Stearic acid | 7 mg. |
| | 350 mg. | are prepared from sufficient bulk quantities by slugging the (S)-2-[[[[3-(benzoylamino)-2-oxo-4-phenylbutyl]methylamino]carbonyl]oxy]-3-phenylpropanoic acid, sodium salt, Avicel, and a portion of the stearic acid. The slugs are ground and passed through a #2 screen, then mixed with the hydrochlorothiazide, lactose, cornstarch, and remainder of the stearic acid. The mixture is compressed into 350 mg. capsule shaped tablets in a tablet press. The tablets are scored for dividing in half.

In a similar manner, tablets can be prepared containing 100 mg. of the product of any of Examples 1 to 20.

What is claimed is:

1. A compound of the formula $$R_3-CH-\underset{\underset{\underset{R_2}{C=O}}{NH}}{CH}-\overset{O}{\overset{\|}{C}}-CH_2-\overset{R_1}{\underset{}{N}}-\overset{O}{\overset{\|}{C}}-Y-\overset{R_4}{\underset{}{CH}}-COOR_5$$

or a pharmaceutically acceptable salt thereof wherein:
Y is oxygen or sulfur;
R₁ is hydrogen, lower alkyl, $$-(CH_2)_n-\bigcirc\!\!\!-, \quad -(CH_2)_n-\bigcirc\!\!\!-_{(R_6)_p},$$

—(CH$_2$)$_n$-cycloalkyl wherein cycloalkyl is a saturated ring of 3 to 7 carbons,

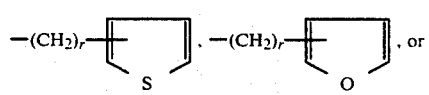 or

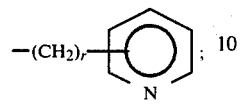

R$_2$ is hydrogen, lower alkyl,

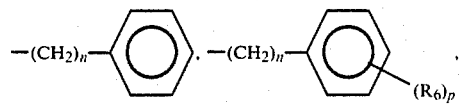

—(CH$_2$)$_n$-cycloalkyl wherein cycloalkyl is a saturated ring of 3 to 7 carbons,

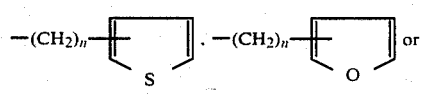 or

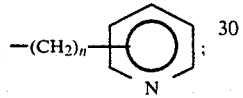

R$_3$ is hydrogen, lower alkyl,

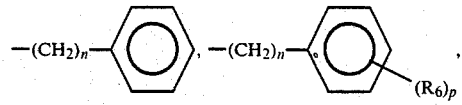

—(CH$_2$)$_n$-cycloalkyl wherein cycloalkyl is a saturated ring of 3 to 7 carbons,

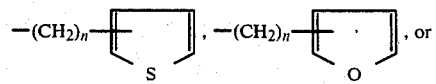 or

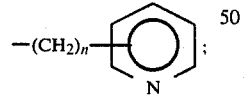

R$_4$ is hydrogen, lower alkyl,

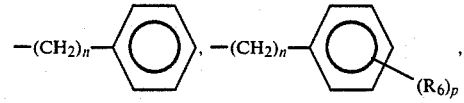

—(CH$_2$)$_n$-cycloalkyl wherein cycloalkyl is a saturated ring of 3 to 7 carbons,

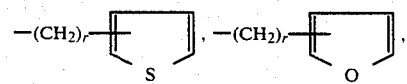

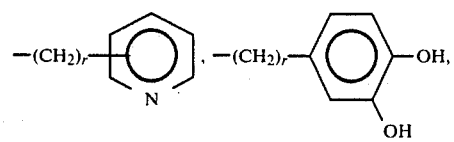

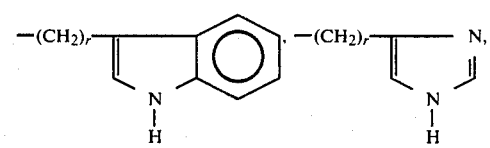

—(CH$_2$)$_r$—NH$_2$, —(CH$_2$)$_r$—SH,

—(CH$_2$)$_r$—S—lower alkyl, 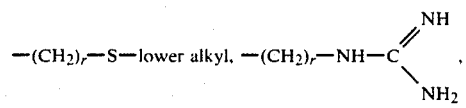

—(CH$_2$)$_r$—C(=O)—NH$_2$, or —(CH$_2$)$_r$—OH;

R$_5$ is hydrogen, lower alkyl, benzyl, benzhydryl, a pharmaceutically acceptable salt forming ion, or

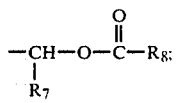

R$_6$ is hydrogen, lower alkyl of 1 to 4 carbons, lower alkoxy of 1 to 4 carbons, lower alkylthio of 1 to 4 carbons, chloro, bromo, fluoro, trifluoromethyl, or hydroxy;

n is zero, one, two, three, or four;

r is one, two, three, or four;

p is one, two, or three provided that p is more than one only if R$_6$ is methyl, methoxy, methylthio, chloro, or fluoro;

R$_7$ is hydrogen, lower alkyl, a saturated cycloalkyl ring of 3 to 7 carbons, or phenyl; and R$_8$ is hydrogen, lower alkyl, lower alkoxy or phenyl.

2. A compound of claim 1 wherein:

R$_1$ is straight or branched chain lower alkyl of 1 to 4 carbons,

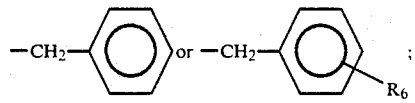

R$_2$ is

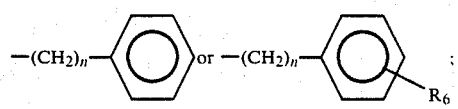

R$_3$ is

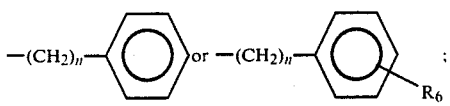

R₄ is straight or branched chain lower alkyl of 1 to 4 carbons, —(CH₂)₄—NH₂, —CH₂—OH,

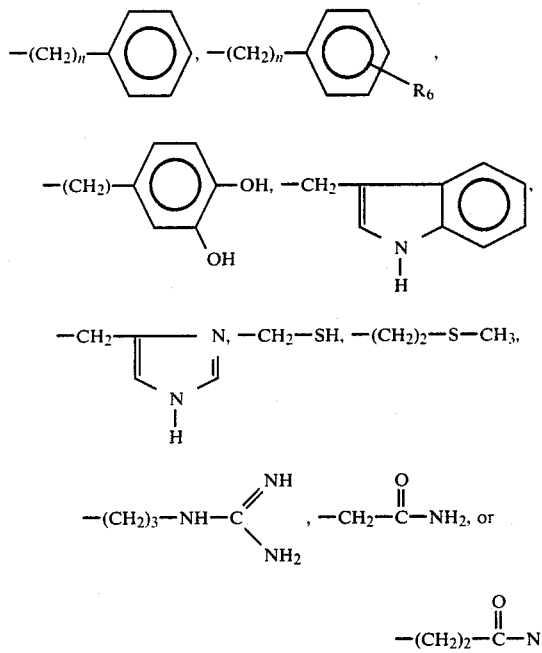

R₅ is hydrogen, an alkali metal salt ion, straight or branched chain lower alkyl of 1 to 4 carbons, or

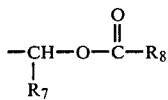

R₆ is methyl, methoxy, methylthio, Cl, Br, F or hydroxy;
n is zero, one, or two;
R₇ is hydrogen, straight or branched chain lower alkyl of 1 to 4 carbons, or cyclohexyl; and
R₈ is straight or branched chain lower alkyl of 1 to 4 carbons or phenyl.

3. A compound of claim 2 wherein Y is sulfur.
4. A compound of claim 2 wherein Y is oxygen.
5. A compound of claim 4 wherein:
R₁ is methyl;
R₂ is phenyl;
R₃ is benzyl;
R₄ is benzyl; and
R₅ is hydrogen or an alkali metal salt ion.

6. The compound of claim 5, (S)-2-[[[[3-(benzoylamino)-2-oxo-4-phenylbutyl]methylamino]carbonyl]oxy]-3-phenylpropanoic acid.

7. A pharmaceutical composition useful for treating hypertension comprising a pharmaceutically acceptable carrier and a hypotensive effective amount of a compound of the formula

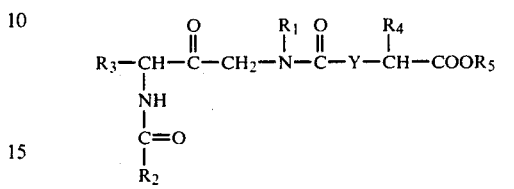

wherein Y, R₁, R₂, R₃, R₄, and R₅ are as defined in claim 1.

8. The method of treating hypertension in a mammalian host which comprises administering an effective amount of the composition of claim 7.

9. A pharmaceutical composition useful as an analgesic comprising a pharmaceutically acceptable carrier and an enkephalinase inhibiting effective amount of a compound of the formula

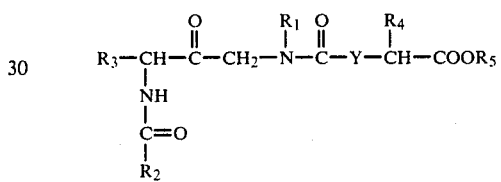

wherein Y, R₂, R₃, R₄ and R₅ are as defined in claim 1; R₁ is branched chain lower alkyl of 3 or 4 carbons,

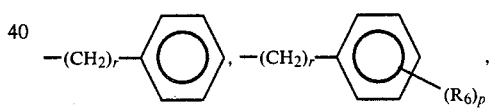

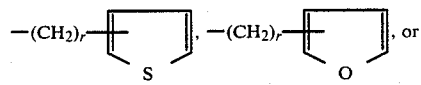

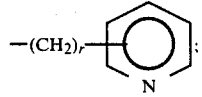

and
r, p, and R₆ are as defined in claim 1.

10. The method of relieving pain in a mammalian host which comprises administering an effective amount of the composition of claim 9.

* * * * *